US007319762B2

(12) United States Patent
Andrea et al.

(10) Patent No.: US 7,319,762 B2
(45) Date of Patent: Jan. 15, 2008

(54) HEADSET WITH FLASHING LIGHT EMITTING DIODES

(75) Inventors: Douglas J. Andrea, Bohemia, NY (US); Qunsheng Liu, Elmhurst, NY (US)

(73) Assignee: Andrea Electronics Corporation, Bohemia, NY (US)

( * ) Notice: Subject to any disclaimer, the term of this patent is extended or adjusted under 35 U.S.C. 154(b) by 0 days.

(21) Appl. No.: 11/482,351

(22) Filed: Jul. 5, 2006

(65) Prior Publication Data

US 2007/0047740 A1 Mar. 1, 2007

Related U.S. Application Data

(60) Provisional application No. 60/710,471, filed on Aug. 23, 2005.

(51) Int. Cl.

| | |
|---|---|
| ***H04B 3/00*** | (2006.01) |
| ***H04R 1/10*** | (2006.01) |
| ***H04R 25/00*** | (2006.01) |
| ***A61B 7/04*** | (2006.01) |
| ***G08B 5/00*** | (2006.01) |

(52) U.S. Cl. .......................... 381/74; 381/77; 381/370; 381/67; 340/815.46

(58) Field of Classification Search .................. 381/77, 381/74, 67, 370, 12, 56, 107, 104; 362/105; 340/815.45, 815.46

See application file for complete search history.

(56) References Cited

U.S. PATENT DOCUMENTS

| | | | | |
|---|---|---|---|---|
| 3,829,856 | A * | 8/1974 | Conroy et al. | 340/815.45 |
| 4,783,813 | A * | 11/1988 | Kempka | 381/67 |
| 5,197,332 | A * | 3/1993 | Shennib | 73/585 |
| 5,751,825 | A * | 5/1998 | Myers et al. | 381/118 |
| 5,791,965 | A | 8/1998 | Kim | |
| 5,928,160 | A * | 7/1999 | Clark et al. | 600/559 |
| 6,002,777 | A * | 12/1999 | Grasfield et al. | 381/67 |
| 6,154,912 | A | 12/2000 | Li | |
| 6,795,718 | B2 | 9/2004 | Bae | |
| 6,918,678 | B2 * | 7/2005 | McClanahan | 362/105 |
| 2002/0064276 | A1 * | 5/2002 | Winegar | 379/430 |
| 2004/0252487 | A1 * | 12/2004 | McCullough et al. | 362/105 |
| 2005/0129259 | A1 * | 6/2005 | Garner | 381/172 |
| 2005/0201569 | A1 * | 9/2005 | Kuraoka et al. | 381/74 |
| 2006/0008106 | A1 * | 1/2006 | Harper | 381/374 |
| 2006/0245598 | A1 * | 11/2006 | Batai | 381/74 |

OTHER PUBLICATIONS www.ipodhacks. com/article.php?sid=1485.* http://www.petersofkensington.com.au/Product/ProductInfo.aspx?id=1601881&cid=557 (one page advertisement for iPod-iDog, release date was Dec. 2006).

(Continued)

*Primary Examiner*—Vivian Chin
*Assistant Examiner*—Devona E. Faulk
(74) *Attorney, Agent, or Firm*—Frommer Lawrence & Haug LLP; Thomas J. Kowalski

(57) ABSTRACT

A headphone system is provided with two earbud headphones and a control module, each fitted with a plurality of light emitting diodes (LEDs). The LEDs may be of many different colors and flash to the beat of the music. Patterns, colors, and intensity may be adjusted based on a user's preferences. The intensity, frequency, and light patterns of the LEDs may change when a threshold level is reached.

10 Claims, 2 Drawing Sheets

40

OTHER PUBLICATIONS http://www.zapwizard.com/MediaPC/IR__Headphone/Headset/Index.html (11 pages of regarding headphones; release date unknown).

http://www.everythingusb.com/digital__age__walk-free__wireless__headphones.html (4 pages regarding headphones; release date estimated at Oct. 2005).

http://downloads.nokiausa.com/userguides/HS3W.PDF (Nokia 2003) (16 pages regarding headset; copyright date of the user's guide is 2003).

http://www.sharperimage.com/us/en/catalog/product/sku__DA111BLU?cm__ven=adwords&cm__cat=Media&cm__pla=audio&cm__ite=ibeat (3 pages regarding advertisement for iBeat product and product manual; copyright date of product manual is 2005).

http://www.sharperimage.com/us/en/catalog/product/sku__SI222RED (6 pages regarding advertisement for iPulse Bear Speaker System and product manual; copyright date of product manual is 2006).

http://www.sharperimage.com/us/en/catalog/product/sku__SI345WHT (9 pages regarding advertisement for iPulse Stereo and product manual; copyright date of product manual is 2006).

* cited by examiner

10

20

HEADSET WITH FLASHING LIGHT EMITTING DIODES

CROSS-REFERENCE TO RELATED APPLICATIONS

This application claims priority from U.S. Provisional Application Ser. No. 60/710,471, filed on Aug. 23, 2005.

BACKGROUND OF THE INVENTION

1. Field of the Invention

The present invention relates to headsets, and more particularly to a headset with flashing light emitting diodes (LEDs).

2. Description of the Related Art

Headphones or headsets are used on a variety of everyday consumer electronics, including, but not limited to, cellular telephones, personal digital assistants (PDAs), portable music players, etc. The user of one of these devices would plug the headset into the device to privately listen to the audio signals output from the device or to listen without disturbing others around the user. The conventional headsets have one or two earphones, and may include a microphone for applications where user audio input is needed, for example, for use with a telephone. A user can, and often does, wear the headset when listening to an audio signal, and even when not.

SUMMARY OF THE INVENTION

Unfortunately, those about the user of a conventional headset can not determine if the user is currently listening to an audio signal just from looking at the user, even though the user is wearing the headset, therefore making it difficult to determine if the user can hear any external noises, comments or questions.

The present invention provides a headset with flashing LEDs that overcomes the problems and deficiencies of the prior art. Thus, in accordance with the present invention, An earbud headphone system is provided comprising one or more ear bud headphones configured to output an audio signal, a plurality of light emitting diodes (LEDs) operably attached to each ear bud headphone and configured to operate as a function of a volume and a rhythm of the audio signal, wherein the intensity and frequency of the LEDs is variable, and a control circuit operable to control which, of a plurality of operation modes, the operation mode the plurality of headphone LEDs operate in as a function of the audio signal. In a normal operation mode, at least one of the plurality of the LEDs may flash in accordance with a beat of the audio signal.

In another embodiment of the earbud headphone system some of the plurality of LEDs may operate as a function of a signal strength and power. In another embodiment, at least one of the plurality of the LEDs indicate a source of the audio signal. The plurality of LEDs may change one or more of color, frequency, intensity, and pattern when a predetermined threshold is exceed.

In another embodiment of the earbud headphone system, when a volume level of the audio input signal reaches a predetermined threshold quantity, the operation mode is changed from a normal operation mode to a saturation mode. When in a saturation mode, at least one of the plurality of the LEDs may flash at a frequency greater than a beat of the audio signal. In another embodiment, in a saturation mode, at least one of the plurality of the LEDs remain illuminated. In a saturation mode, an intensity of at least one of the plurality of the LEDs may remain at an increased state. Furthermore, in a saturation mode, at least one of the plurality of the LEDs may change color, frequency, and intensity.

In another embodiment of the headphone system, a control module may be operably connected to the at least one headphones. The control module may comprise a microphone and a plurality of LEDs.

In another embodiment of the headphone system, a night use mode is utilized. The brightness of at least one of the plurality of the LEDs may be configured to remain at an increased intensity and the audio signal may be output at a decreased volume when sound is detected by the microphone.

In yet another embodiment of the headphone system, the system can be utilized as a fashion accessory. The color of at least one of the plurality of LEDs may be changed to colors of the user's preference.

In a further embodiment of the headphone system, the system can be used to monitor the volume level of the output. The change of one or more of color, frequency, intensity, and pattern of at least one of the plurality of LEDs can be related to the volume level, allowing a non-user to observe the LEDs and understand the volume level at which the headset is operating.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENT

Figure 1:
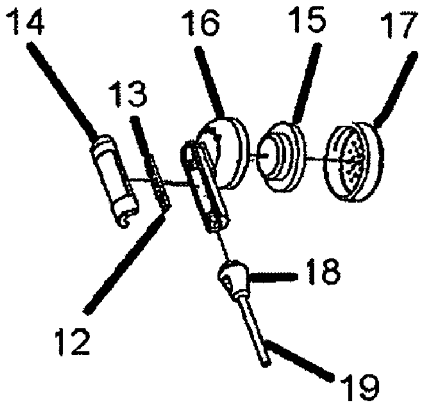
FIG. 1 is a diagram of an earphone fitted with LEDs according to the present invention.

Hereinafter, preferred embodiments of the present invention will be described with reference to the accompanying drawings. It should be noted that the similar components are designated by similar reference numerals although they are illustrated in different drawings. Also, in the following description, a detailed description of known functions and configurations incorporated herein will be omitted when it may obscure the subject matter of the present invention.

The present invention proposes a headset having LEDs thereon that turn on and off according to audio characteristics of an input audio signal. The LEDs serve as both a visual enhancement to the headset as well as to alert others that the user of the headset is listening to an audio signal.

FIG. 1 is a diagram of an earphone 10 fitted with LEDs 12 according to the present invention. The earphone 10 is made up of a speaker 15 encased in a housing 16 and covered by a speaker cover 17. The LEDs 12 are operably connected to a circuit board 13 located beneath a LED cover 14. An external cable 19 operable to carry an audio signal to the LEDs 12 and speaker 15 is connected to the LEDs 12 and speaker 15 by means of a cable support 18 attached to the housing 16.

Although FIG. 1 shows three LEDs in a straight line pattern, any number of LEDs 12 may be present and may be configured in any pattern. And although earphone headphones are shown, the present invention may be configured with any type of headphone. The headphones may be any color and may of any material.

Figure 2:
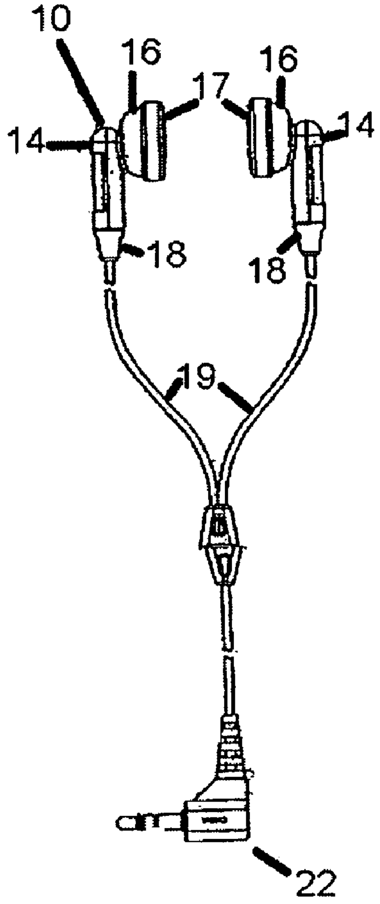
FIG. 2 is a diagram of a headset with two earphones and an audio input jack according the present invention.

FIG. 2 is a diagram of a headset with two earphones 10 and an audio input 22 according one embodiment of the present invention. In addition to the two earphones 10, an audio input 22 is included. The audio input 22 is operable to plug into any device that outputs an audio signal. The LEDs 12 and speakers 15 are not shown, but are located in the housing 16.

Figure 3:
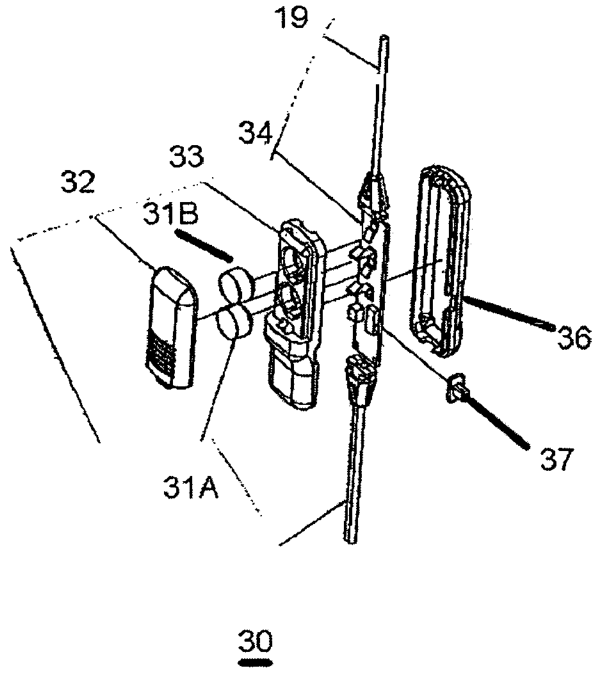
FIG. 3 is a diagram of a control module according to one embodiment of the present invention.

FIG. 3 shows a diagram of a control module 30 according to another embodiment of the present invention. The control module 30 is located between the audio input 22 and the earphones 10. The control module 30 may be made up of a housing 33 that operably fits over the circuit board 34. The circuit board 34 contains the control circuitry. Attached to the circuit board 34, elements 31*a* and 31*b* are located beneath a cover portion 32. A rear cover portion 36 attaches to the back. A switch 37 is operably attached to the circuit board 34 and is configured to power on/off the control module.

In one embodiment, both elements 31*a* and 31*b* may be LEDs. However, in another embodiment, one of elements 31 may be a mic. Additionally located on the circuit board 34 is a battery.

Although two LEDs 31 are shown, any number of LEDs 31 may be located on the control module 30. The LEDs may be configured to face any direction and be placed in any direction.

The LEDs 31 may be controlled by a control circuit on circuit board 34 in similar fashion as those of the earphone 10.

In FIG. 3, although one switch 37 is shown and is located on a side portion of the control module, any number of switches may be used. For example, a second switch may be configured to power on/off the LEDs 31 and/or mic.

Figure 4:
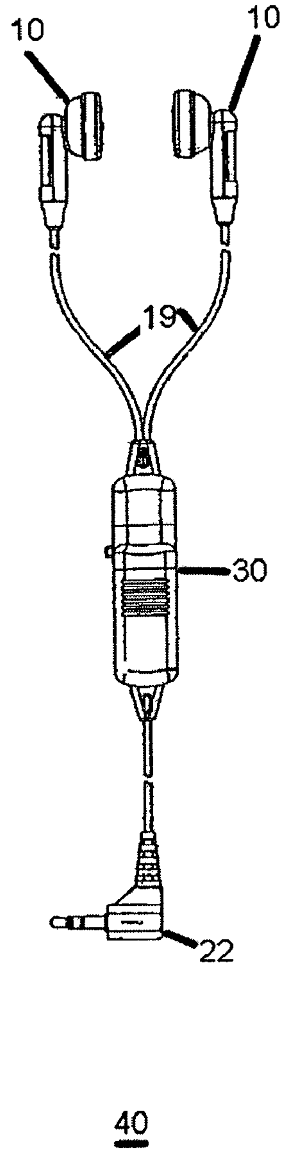
FIG. 4 is a diagram of a headphone system according to one embodiment of the present invention.

FIG. 4 shows a complete headphone system according to one embodiment of the present invention. Control module 30 is 30 is operably connected, via the cables 19, in between the audio input 22 and the two earphone 10 fitted headset.

A control circuit may be located on the circuit board 13 located in each earphone 10 and in control module 30 on circuit board 34. One control circuit may exist and operable to control LEDs 12, 31. However, an independent control circuit may be located in each earphone and in control module 30.

Each control circuit is operable to receive the input signal and configured to control the LEDs. The LEDs 12, 31 may be of any color and controlled to vary in frequency and intensity. Additionally, a pattern created by the lit LEDs 12, 31 may vary and be configured to be an indicator of any number of functions. The LEDs 12, 31 may be controlled to operate as a function of the volume, rhythm, signal strength, and/or power of the audio signal.

In one embodiment of the present invention, a number of modes exist. In a normal operation mode, the control circuit may control the LEDs 12, 31 to flash in accordance with a beat of the music in the audio signal. The colors of the LEDs 12, 31 and the patterns in which they flash may vary and may be adjusted according to a user's preferences. The intensity of the LEDs 12, 31 may vary as a function of a volume of the audio signal.

Furthermore, in a normal operation mode, at least one LED may be designated to indicate a source of the audio signal. For example, the designated LED or LEDs may vary in frequency, color, or intensity when the audio signal is a cell phone conversation. One of more LEDs may also be designated to indicate the presence of an audio signal. For example, when a user is not listening to music or having a conversation, the designated LEDs may change frequency, color or intensity.

Additionally, the control circuit may operate in a saturation mode. In the saturation mode, the LEDs 12, 31 may change color, frequency, intensity, and/or pattern when a threshold is reached. For example, when the volume of the audio signal reaches a threshold level, the boost circuit may operate in saturation mode. Additionally, the boost circuit 13 may operate in saturation mode based on signal strength, power and the length of use, a song, or a conversation. In another embodiment, the control circuit may operate in a night use mode. In a night use mode, the brightness of the LEDs 12, 31 are configured to remain at an increased intensity and the audio signal is output at a decreased volume. Using the mic, the volume may be lowered when sound is detected.

Furthermore, in saturation mode, at least one of the plurality of the LEDs flashes at a frequency greater than a beat of the audio signal. In another embodiment, in saturation mode, at least one of the plurality of LEDs remains illuminated. In yet another embodiment, in saturation mode, an intensity of at least one of the plurality of the LEDs remains at an increased state.

The headphone system can be utilized as a fashion accessory. For example, the color of at least one of the plurality of LEDs can be changed to colors of the user's preference. The color of at least one of the plurality of LEDs can be changed to match, accent or contrast the user's apparel, or to signify a specific holiday or holiday season, i.e., the fourth of July or Halloween. The color of at least one of the plurality of LEDs can also be changed at will by the user.

The headphone system can additionally be used to monitor the volume level of the output. The change of one or more of color, frequency, intensity, and pattern of at least one of the plurality of LEDs can be related to the volume level, allowing a non-user to observe the LEDs and understand the volume level at which the headset is operating. For example, a parent can monitor the volume level of a headset used by a child by observing one or more of the LEDs for a specific color, frequency, pattern or intensity that signifies the headset is functioning at a specific volume or decibel level, or that the headset is functioning within a preset range of volume or decibel levels. Alternatively, the user can similarly monitor the volume or decibel level by similarly observing the one or more LEDs.

While illustrative embodiments of the invention have been described above, it is, of course, understood that various modifications will be apparent to those of ordinary skill in the art. Such modifications are within the spirit and scope of the invention, which is limited and defined only by the appended claims.

What is claimed is:

1. An earbud headphone system comprising:

one or more ear bud headphones configured to output an audio signal;

a plurality of light emitting diodes (LEDs) operably attached to each ear bud headphone and configured to operate as a function of a volume and a rhythm of the audio signal, wherein the intensity and frequency of the LEDs is variable; and a control circuit operable to control which, of a plurality of operation modes, the operation mode the plurality of headphone LEDs operate in as a function of the audio signal; and wherein:

when a volume level of the audio input signal reaches a predetermined threshold quantity, the operation mode is changed from a normal operation mode to a saturation mode; and in the saturation mode, at least one of the plurality of LEDs change color, frequency, intensity or pattern, or flash at a frequency greater than a beat of the audio signal.

2. The earbud headphone system of claim 1, wherein the plurality of LEDs operate as a function of a signal strength and power.

3. The earbud headphone system of claim 1, wherein the plurality of LEDs change one or more of color, frequency, intensity, and pattern when a predetermined threshold is exceed.

4. The earbud headphone system of claim 1, wherein, in a normal operation mode, at least one of the plurality of the LEDs flash in accordance with a beat of the audio signal.

5. The earbud headphone system of claim 1, wherein at least one of the plurality of the LEDs indicate a source of the audio signal.

6. The earbud headphone system of claim 1, wherein, in the saturation mode, at least one of the plurality of the LEDs remain illuminated.

7. The earbud headphone system of claim 1, wherein, in the saturation mode, an intensity of at least one of the plurality of the LEDs remains at an increased state.

8. The earbud headphone system of claim 1, wherein, in the saturation mode, at least one of the plurality of the LEDs change color, frequency, and intensity.

9. The earbud headphone system of claim 1, further comprising:

a control module operably connected to the at least one headphone comprising a microphone and a plurality of LEDs.

10. The earbud headphone system of claim 9, wherein, in a night use mode, the plurality of the LEDs operate as a function of the ambient audio signals detected by the microphone.

* * * * *